US00PP24045P2

(12) United States Plant Patent
Marczyński

(10) Patent No.: US PP24,045 P2
(45) Date of Patent: Nov. 26, 2013

(54) ***CLEMATIS* PLANT NAMED 'DIAMOND BALL'**

(50) Latin Name: *Clematis hybrida*
Varietal Denomination: Diamond Ball

(75) Inventor: Szczepan Marczyński, Pruszków (PL)

(73) Assignee: Spring Meadow Nursery Inc., Grand Haven, MI (US)

( * ) Notice: Subject to any disclaimer, the term of this patent is extended or adjusted under 35 U.S.C. 154(b) by 82 days.

(21) Appl. No.: 13/385,281

(22) Filed: Feb. 10, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

(56) References Cited

PUBLICATIONS

PLUTO Plant Variety Database 2012-06. Search for Diamond Ball.*

* cited by examiner

*Primary Examiner* — Annette Para
(74) *Attorney, Agent, or Firm* — C. A. Whealy

(57) ABSTRACT

A new and distinct cultivar of *Clematis* plant named 'Diamond Ball' characterized by its upright, relatively compact and vining plant habit; freely flowering habit; long flowering period; and semi-double to double violet blue-colored flowers.

1 Drawing Sheet

Botanical designation: *Clematis hybrida.*
Cultivar denomination: 'DIAMOND BALL'.

BACKGROUND OF THE INVENTION

The present invention relates to a new and distinct cultivar of *Clematis* plant, botanically known as *Clematis hybrida* and hereinafter referred to by the name 'Diamond Ball'.

The new *Clematis* plant originated from an open-pollination in Pruszków, Poland of an unidentified selection of *Clematis hybrida*, not patented, as the female, or seed parent with an unknown selection of *Clematis hybrida*, as the male, or pollen, parent. The new *Clematis* plant was discovered and selected by the Inventor as a single flowering plant in a controlled environment in Pruszków, Poland in 1999.

Asexual reproduction of the new *Clematis* plant by cuttings in Pruszków, Poland since June, 2001 has shown that the unique features of this new *Clematis* plant are stable and reproduced true to type in successive generations.

SUMMARY OF THE INVENTION

Plants of the new *Clematis* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Diamond Ball'. These characteristics in combination distinguish 'Diamond Ball' as a new and distinct *Clematis* plant:

1. Upright, relatively compact and vining plant habit.
2. Freely flowering habit.
3. Long flowering period.
4. Semi-double to double violet blue-colored flowers.

Plants of the new *Clematis* differ primarily from plants of the female parent selection in plant habit and flower form.

Plants of the new *Clematis* can be compared to plants of the *Clematis* 'Belle of Woking', not patented. Plants of the new *Clematis* differ primarily from plants of 'Belle of Woking' in the following characteristics:

1. Plants of the new *Clematis* are more compact than plants of 'Belle of Woking'.
2. Plants of the new *Clematis* are more freely branching than plants of 'Belle of Woking'.
3. Plants of the new *Clematis* are more freely flowering than plants of 'Belle of Woking'.
4. Plants of the new *Clematis* have more sepals per flower than plants of 'Belle of Woking'.
5. Plants of the new *Clematis* and 'Belle of Woking' differ in flower color.

Plants of the new *Clematis* can also be compared to plants of the *Clematis* 'Chalcedony', not patented. Plants of the new *Clematis* differ primarily from plants of 'Chalcedony' in the following characteristics:

1. Plants of the new *Clematis* are more compact than plants of 'Chalcedony'.
2. Plants of the new *Clematis* and 'Chalcedony' differ in flower color.

BRIEF DESCRIPTION OF THE PHOTOGRAPH

The accompanying colored photograph illustrates the overall appearance of the new *Clematis* plant showing the colors as true as it is reasonably possible to obtain in colored reproductions of this type. Colors in the photograph may differ slightly from the color values cited in the detailed botanical description which accurately describe the actual colors of the new *Clematis* plant.

The photograph comprises a side perspective view of a typical flowering plant of 'Diamond Ball' grown in an outdoor nursery.

DETAILED BOTANICAL DESCRIPTION

Plants used for the aforementioned photograph and following description were grown during the summer in an outdoor nursery in Pruszków, Poland and under cultural practices which closely approximate commercial production. During the production of the plants, day temperatures ranged from 18° C. to 23° C. and night temperatures ranged from 13° C. to 16° C. Plants were three years old when the photograph and the description were taken. In the following description, color references are made to The Royal Horticultural Society Colour Chart, 1995 Edition, except where general terms of ordinary dictionary significance are used.

Botanical classification: *Clematis hybrida* 'Diamond Ball'.

Parentage:

*Female, or seed, parent*.—Unidentified selection of *Clematis hybrida*, not patented.

*Male, or pollen, parent*.—Unknown selection of *Clematis hybrida*, not patented.

Propagation:

*Type*.—By cuttings.

*Time to initiate roots, summer*.—About 21 days.

*Time to produce a rooted young plant, summer*.—About 45 to 120 days.

*Root description*.—Fine to thick; color, close to 163A.

*Rooting habit*.—Freely branching.

Plant description:

*Plant and growth habit*.—Perennial vine; upright, relatively compact and vining plant habit; moderately vigorous growth habit.

*Plant height*.—About 200 cm.

*Plant width*.—About 100 cm.

*Lateral branch description*.—Branching habit: Freely branching habit, about 14 to 20 lateral branches develop per plant. Length: About 10 cm to 35 cm. Diameter: About 2 mm to 3 mm. Internode length: About 8 cm to 12 cm. Texture, developing: Slightly pubescent. Texture, developed: Smooth, glabrous. Color, developing: Close to 59A. Color, developed: Close to 175C.

Foliage description:

*Arrangement*.—Opposite, simple or compound with three leaflets.

*Length, single leaf*.—About 7 cm to 12 cm.

*Length, leaflet*.—About 9 cm.

*Width, single leaf*.—About 4 cm to 6 cm.

*Width, leaflet*.—About 4 cm to 5 cm.

*Shape, single leaf*.—Cordate.

*Shape, leaflet*.—Ovate.

*Apex, single leaf*.—Apiculate.

*Apex, leaflet*.—Apiculate.

*Base, single leaf*.—Cordate.

*Base, leaflet*.—Truncate.

*Margin, single leaves and leaflets*.—Entire.

*Texture, single leaves and leaflets, upper surface*.—Smooth, glabrous.

*Texture, single leaves and leaflets, lower surface*.—Pubescent.

*Venation pattern, single leaves and leaflets*.—Pinnate.

*Color, single leaves and leaflets*.—Developing, upper surface: Close to 143A. Developing, lower surface: Close to 143B. Fully expanded, upper surface: Close to 137A to 137B; venation, close to 137A to 137B. Fully expanded, lower surface: Close to 138A; venation, close to 138A.

*Petioles*.—Length, single leaves: About 5 cm to 8 cm. Length, leaflets: About 1.5 cm to 3 cm. Diameter, single leaves and leaflets: About 1 mm to 2 mm. Color, single leaves and leaflets, upper surface: Close to 187A. Color, single leaves and leaflets, lower surface: Close to 148B.

Flower description:

*Flower shape, arrangement and flowering habit*.—Semi-double to double rotate terminal and axillary flowers; flowers face outwardly; freely flowering habit, about 50 flowers develop per plant.

*Natural flowering season*.—Continuous flowering from June to August in Poland.

*Flower longevity on the plant*.—About five to ten days; flowers persistent.

*Fragrance*.—None detected.

*Flower buds*.—Length: About 2 cm. Diameter: About 2 cm. Shape: Ovate. Color: Close to 145A to 145C.

*Flowers*.—Diameter: About 6 cm to 8 cm. Depth (height): About 3 cm to 4 cm.

*Petals*.—None observed.

*Sepals*.—Arrangement: About 35 to 40 in about three to six whorls. Length: About 1 cm to 4 cm. Width: About 1.5 cm to 2 cm. Shape: Elliptic to oval. Apex: Aristate. Base: Cuneate. Margin: Entire, undulate. Texture, upper and lower surfaces: Smooth, glabrous. Color: When opening, upper surface: Close to 85C; central stripe, close to 155B. When opening, lower surface: Close to 85D; central stripe, close to 157A. Fully opened, upper and lower surfaces: Close to 92D; central stripe, close to 155C.

*Peduncles*.—Length: About 3 cm to 8 cm. Diameter: About 2 mm to 3 mm. Strength: Strong. Texture: Smooth, glabrous. Color: Close to 145A.

*Reproductive organs*.—Stamens: Quantity per flower: About 30 to 40. Anther shape: Lanceolate. Anther length: About 5 mm. Anther color: Close to 154C. Pollen amount: Scarce. Pollen color: Close to 154D. Pistils: Quantity per flower: About 50 to 70. Pistil length: About 1.5 cm. Stigma shape: Conical, narrow. Stigma color: Close to 155C. Style length: About 1.5 cm. Style color: Close to 145C. Ovary color: Close to 145C.

*Seeds*.—Length: About 2.5 cm. Diameter: About 2.5 mm to 3 mm. Color, immature: Close to 144C. Color, mature: Close to 166C.

Disease & pest resistance: Plants of the new *Clematis* have not been noted to be resistant to pathogens and pests common to *Clematis* plants.

Garden performance: Plants of the new *Clematis* have exhibited good tolerance to rain and wind and have been observed to be suitable for USDA Hardiness Zone 5 and USDA Heat Zone 9.

It is claimed:

1. A new and distinct *Clematis* plant named 'Diamond Ball' as illustrated and described.

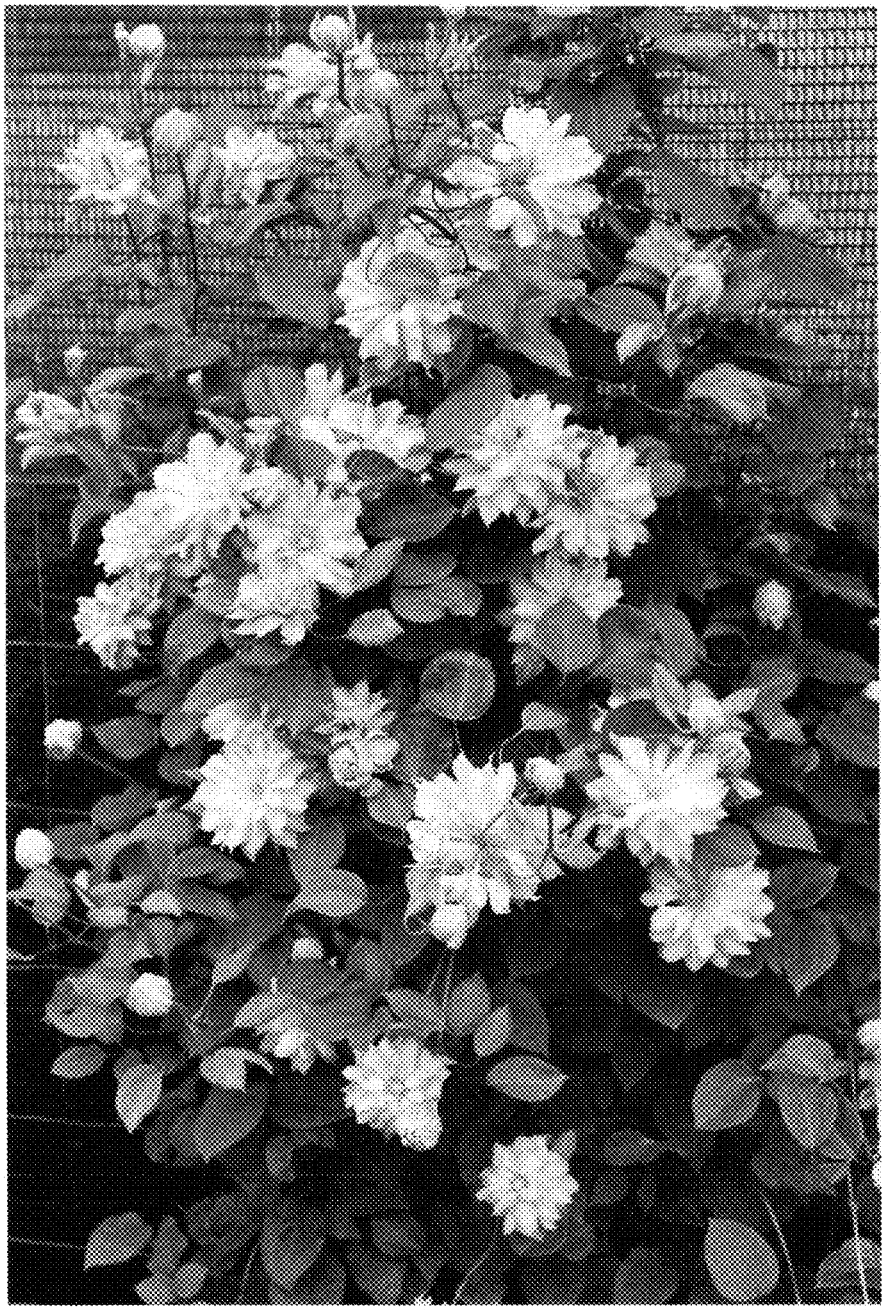

* * * * *